(12) United States Patent
Simon et al.

(10) Patent No.: US 9,974,724 B1
(45) Date of Patent: May 22, 2018

(54) ORAL CARE COMPOSITIONS WITH INCREASED WHITENING EFFICACY

(71) Applicant: COLGATE-PALMOLIVE COMPANY, New York, NY (US)

(72) Inventors: Eric Simon, Somerset, NJ (US); Venda Porter-Maloney, Piscataway, NJ (US); Vyoma Patel, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days. days.

(21) Appl. No.: 15/336,460

(22) Filed: Oct. 27, 2016

(51) Int. Cl.
*A61Q 11/00* (2006.01)
*A61K 8/27* (2006.01)
*A61K 8/362* (2006.01)
*A61K 8/36* (2006.01)
*A61K 8/92* (2006.01)
*A61K 8/21* (2006.01)
*A61K 8/49* (2006.01)

(52) U.S. Cl.
CPC ............... *A61K 8/362* (2013.01); *A61K 8/21* (2013.01); *A61K 8/27* (2013.01); *A61K 8/36* (2013.01); *A61K 8/4926* (2013.01); *A61K 8/92* (2013.01); *A61Q 11/00* (2013.01); *A61K 2800/43* (2013.01)

(58) Field of Classification Search
CPC .......... A61K 8/27; A61K 45/06; A61K 33/30; A61Q 11/00
See application file for complete search history.

(56) References Cited

U.S. PATENT DOCUMENTS

| | | | |
|---|---|---|---|
| 5,130,122 A * | 7/1992 | Tabibi | A61K 8/06 424/49 |
| 6,582,682 B2 | 6/2003 | Stier | |
| 2007/0020201 A1 | 1/2007 | Boyd et al. | |
| 2013/0078198 A1* | 3/2013 | Aitken | A61K 8/27 424/56 |
| 2013/0231302 A1* | 9/2013 | Raad | A61L 2/186 514/54 |
| 2013/0236400 A1 | 9/2013 | Lewus et al. | |

FOREIGN PATENT DOCUMENTS

| | | | |
|---|---|---|---|
| CN | 105686979 A | 6/2016 | |
| DE | 102010031291 | 1/2012 | |
| WO | WO 2014098888 A1 * | 6/2014 | ............... A61K 8/24 |
| WO | WO 2014/184084 | 11/2014 | |
| WO | WO 2015/095709 A1 | 6/2015 | |
| WO | WO-2015095709 A1 * | 6/2015 | ............... A61K 8/25 |
| WO | WO 2015/099642 A1 | 7/2015 | |

OTHER PUBLICATIONS

International Search Report and Written Opinion in International Application No. PCT/US2016/059147, dated Feb. 7, 2017.

* cited by examiner

*Primary Examiner* — Tracy Liu

(57) ABSTRACT

A dual-phase mouthwash composition for whitening teeth is disclosed. The dual-phase mouthwash composition includes an orally acceptable vehicle having a hydrophilic phase and a hydrophobic phase, a blue dye and/or blue pigment having a blue to blue-violet color with a hue angle in the CIELAB system from about 200 to about 320 degrees, and a zinc salt.

14 Claims, No Drawings

ORAL CARE COMPOSITIONS WITH INCREASED WHITENING EFFICACY

BACKGROUND

As is known in the art, the visual perception of a white substance can be altered through the deposition of a blue pigment and/or a blue dye. This effect is commonly used in laundry detergent products to make white clothes appear "whiter" to the human eye. This effect has also been applied to oral care products (e.g., toothpastes). For example, the blue dye and/or the blue pigment added to the oral care products may be deposited onto teeth, thereby allowing the off-white and/or yellow color of the teeth to appear whiter to the human eye.

While these oral care products provide effective whitening after only a single use, the blue dye and/or the blue pigment may only remain deposited on the teeth for a limited duration, thereby allowing the yellow stains to eventually reappear. Increasing the relative concentration of blue dye and/or blue pigment delivered to the teeth may increase the duration of deposition on the teeth and/or improve the perceived whiteness of the teeth. Accordingly, improved oral care compositions and methods for increasing the relative concentration of blue dye and/or blue pigment delivered to the teeth are desired.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a dual-phase mouthwash composition, including an orally acceptable vehicle having a hydrophilic phase and a hydrophobic phase, a blue dye and/or blue pigment having a blue to blue-violet color with a hue angle in the CIELAB system from about 200 to about 320 degrees, and a zinc salt.

In another embodiment, the zinc salt is selected from zinc lactate and zinc citrate.

In another embodiment, the dual-phase mouthwash composition includes about 0.10 wt % to about 1.0 wt %, optionally about 0.25 wt % to about 0.30 wt %, further optionally about 0.28 wt % of the zinc salt.

In another embodiment, the zinc salt is zinc lactate.

In another embodiment, the zinc salt is zinc citrate.

In another embodiment, the dual-phase mouthwash composition includes about 0.0008 wt % to about 0.0020 wt %, optionally about 0.0010 wt % to about 0.0018 wt %, further optionally about 0.0012 wt % to about 0.0016 wt % of the blue dye and/or the blue pigment.

In another embodiment, the blue dye and/or the blue pigment includes a dye, and at least a portion of the dye is dispersed in the hydrophobic phase of the orally acceptable vehicle.

In another embodiment, the blue dye and/or the blue pigment includes a dye, and at least a portion of the dye is dispersed in the hydrophilic phase of the orally acceptable vehicle.

In another embodiment, the blue dye and/or the blue pigment includes one of CI Food Blue 5, FD&C Blue No. 1, D&C Green No. 6, and D&C Violet No. 2.

In another embodiment, the hydrophobic phase includes white mineral oil.

In another embodiment, the dual-phase mouthwash composition further includes a fluoride ion source, optionally the fluoride ion source includes sodium fluoride.

In another embodiment, the dual-phase mouthwash composition further includes an antibacterial agent, optionally the antibacterial agent is cetylpyridinium chloride (CPC).

In another embodiment, the dual-phase mouthwash composition is free of peroxides.

In another embodiment, the dual-phase mouthwash composition further includes a hydrotrope.

The foregoing and/or other aspects and utilities embodied in the present disclosure may also be achieved by providing a method of whitening teeth, including contacting a dual-phase mouthwash composition to a surface of the teeth, where the dual-phase mouthwash includes an orally acceptable vehicle having a hydrophilic phase and a hydrophobic phase, a blue dye and/or blue pigment having a blue to blue-violet color with a hue angle in the CIELAB system from about 200 to about 320 degrees, and a zinc salt.

The foregoing and/or other aspects and utilities embodied in the present disclosure may be achieved by providing a dual-phase mouthwash composition substantially as hereinbefore described, with reference to the examples and excluding, if any, comparative examples.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Compositions

The present inventors have surprisingly and unexpectedly discovered that oral care compositions including a blue dye and/or a blue pigment and zinc enhance whitening efficacy of teeth. The present inventors have also surprisingly and unexpectedly discovered that oral care products (e.g., dual-phase mouthwashes) or the oral care compositions thereof, including a hydrophilic phase, a hydrophobic phase, zinc, and a blue dye and/or a blue pigment, when combined with one another, exhibit a synergistic effect and provide a significant and unexpected increase in whitening efficacy over conventional oral care products or conventional oral care compositions thereof without the zinc. Without being bound by theory, it is believed that the zinc may prolong the duration in which blue dye and/or blue pigment may be deposited on the teeth by facilitating or enhancing the deposition of blue dye and/or blue pigment on the teeth. For example, the zinc may facilitate the deposition of the blue dye and/or the blue pigment on surfaces of the teeth. Accordingly, the oral care compositions disclosed herein may have relatively greater or enhanced whitening efficacy and/or duration as compared to the conventional oral care compositions that include blue dye and/or blue pigment without the zinc. Additionally, in view of the enhanced whitening efficacy and/or duration, the oral care compositions, and the oral care products incorporating the oral care compositions, may include reduced amounts of blue dye and/or blue pigment without a concomitant decrease in whitening efficacy. As further described herein, the oral care compositions may form at least a portion of or be used in one or more oral care products (e.g., mouthwash).

Zinc

The oral care composition may include zinc. The zinc of the oral care composition may be or include a zinc ion and/or one or more zinc salts. For example, the zinc salts may at least partially dissociate in an aqueous solution to produce zinc ions. Illustrative zinc salts may include, but are not limited to, zinc lactate, zinc oxide, zinc chloride, zinc phosphate, zinc citrate, zinc acetate, zinc borate, zinc butyrate, zinc carbonate, zinc formate, zinc gluconate, zinc glycerate, zinc glycolate, zinc oxide, zinc phosphate, zinc picolinate, zinc proprionate, zinc salicylate, zinc silicate, zinc stearate, zinc tartrate, zinc undecylenate, and mixtures thereof. In a preferred embodiment, the zinc salt is zinc lactate.

The amount of the zinc ion or the zinc salt included in the oral care composition may widely vary. For example, the amount of the zinc ion or the zinc salt may be from about 0.05 wt %, about 0.10 wt %, about 0.15 wt %, about 0.20 wt %, about 0.25 wt %, about 0.30 wt %, about 0.35 wt %, about 0.40 wt %, about 0.45 wt %, about 0.50 wt %, about 0.55 wt %, or about 0.60 wt % to about 0.70 wt %, about 0.75 wt %, 1.0 wt %, about 1.5 wt %, about 2.0 wt %, about 2.5 wt %, about 3.0 wt %, about 3.5 wt %, 4.0 wt %, about 4.5 wt %, about 5.0 wt %, or about 5.5 wt %. In another example, the amount of the zinc ion or the zinc salt may be about 0.1 wt % to about 5 wt %, about 0.2 wt % to about 4.0 wt % about 0.30 wt % to about 3.0 wt %, about 0.40 wt % to about 2.0 wt %, or about 0.50 wt % to about 1.0 wt %. The zinc ion or the zinc salt may also be present in the compositions of the present disclosure in an amount from about 0.10 wt % to about 1.0 wt %, about 0.50 wt % to about 1.5 wt %, about 1.0 wt % to about 2.0 wt %, about 1.5 wt % to about 2.5 wt %, or about 2.0 wt % to about 3.0 wt %. In an exemplary embodiment, the oral care composition may include at least 0.25 wt % of the zinc salt. In another embodiment, the amount of the zinc salt in the oral care composition may be from about 0.25 wt % to about 0.30 wt %. For example, the oral care composition may include about 0.28 wt % of zinc lactate. In another example, the oral care composition may include about 0.28 wt % of zinc citrate. In an exemplary embodiment, the oral care composition may include at least 0.040 wt % of the zinc ion. For example, the oral care composition may include at least 0.040 wt %, at least 0.045 wt %, at least 0.050 wt %, at least 0.055 wt %, at least 0.060 wt %, at least 0.065 wt %, at least 0.070 wt %, or at least 0.075 wt %. In another example, the amount of the zinc ion in the oral care composition may be from about 0.030 wt % to about 0.100 wt %, about 0.035 wt % to about 0.095 wt %, about 0.040 wt % to about 0.090 wt %, about 0.045 wt % to about 0.085 wt %, about 0.050 wt % to about 0.080 wt %, about 0.055 wt % to about 0.075 wt %, about 0.060 wt % to about 0.070 wt %, about 0.062 wt % to about 0.069 wt %, or about 0.064 wt % to about 0.067 wt %. For example, the oral care composition may include about 0.066 wt % of the zinc ion.

Blue Dye and/or Blue Pigment

The oral care composition may include one or more blue dye and/or blue pigment. The blue dye and/or the blue pigment may be a substance in the form of a solid (e.g., a dry powder) or a fluid (e.g., a liquid) that imparts color to another substance or substrate.

The amount of any one or more of blue dye and/or blue pigment included in the oral care composition may widely vary. For example, the amount of any one or more of blue dye and/or blue pigment in the oral care composition may be from about 0.0006 wt %, about 0.0007 wt %, about 0.0008 wt %, about 0.0009 wt %, about 0.0010 wt %, about 0.0011 wt %, about 0.0012 wt %, about 0.0013 wt %, about 0.0014 wt %, about 0.0015 wt %, about 0.0016 wt %, about 0.0017 wt %, about 0.0018 wt %, or about 0.0019 wt % to about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %, about 0.0080 wt %, or greater. In another example, the amount of any one or more of blue dye and/or blue pigment in the oral care composition may be about 0.0006 wt % to about 0.0022 wt %, about 0.0007 wt % to about 0.0021 wt %, about 0.0008 wt % to about 0.0020 wt %, about 0.0009 wt % to about 0.0019 wt %, about 0.0010 wt % to about 0.0018 wt %, about 0.0011 wt % to about 0.0017 wt %, about 0.0012 wt % to about 0.0016 wt %, or about 0.0013 wt % to about 0.0015 wt %. In a preferred embodiment, the amount of any one or more of blue dye and/or blue pigment in the oral care composition may be about 0.0008 wt % to about 0.0020 wt %, about 0.0010 wt % to about 0.0018 wt %, or about 0.0012 wt % to about 0.0016 wt %. For example, the amount of any one or more of the blue dye and/or the blue pigment in the oral care composition may be about 0.0014 wt %. In another example, the amount of any one or more of the blue dye and/or the blue pigment in the oral care composition may be about 0.0010 wt % to about 0.0090 wt %, about 0.0020 wt % to about 0.0080 wt %, about 0.0030 wt % to about 0.0070 wt %, or about 0.0040 wt % to about 0.0060 wt %. In another example, the amount of any one or more of the blue dye and/or the blue pigment in the oral care composition may be about 0.00001 wt % to about 0.00015 wt %, about 0.00002 wt % to about 0.00014 wt %, about 0.00003 wt % to about 0.00013 wt %, about 0.00004 wt % to about 0.00012 wt %, about 0.00005 wt % to about 0.00011 wt %, about 0.00006 wt % to about 0.00010 wt %, or about 0.00007 wt % to about 0.00009 wt %. In another example, a total amount of all the blue dye and/or the blue pigment in the oral care composition may be about 0.0020 wt % to about 0.0100 wt %, about 0.0030 wt % to about 0.0090 wt %, about 0.0040 wt % to about 0.0080 wt %, about 0.0055 wt % to about 0.0075 wt %, or about 0.0060 to about 0.0070 wt %. For example, a total amount of the blue dye and/or the blue pigment included in the oral care composition may be about 0.0065 wt %.

Pigments

As previously discussed, the oral care composition may include one or more pigments. As used herein, the term "pigment" may refer to a synthetic or natural water insoluble substance, which imparts color to another substance. The one or more pigments may be configured to enhance the whiteness of the teeth. For example, the pigments may be deposited on a surface of the teeth to alter the visually perceived whiteness of the teeth.

The one or more pigments may have a hue angle, in the CIELAB scale, of from about 200 degrees to about 320 degrees. For example, the pigments may have a hue angle between about 250 and about 290 degrees. It should be appreciated that "CIELAB" is a color measurement system or standard adopted by the Commission Internationale de l'Eclairage (CIE) in 1976. It is based on a three-dimensional CIELAB color space. The system was developed to represent color in a manner that is consistent with human vision and proportional to perceived color differences. CIELAB values describe coordinates of a specific color in the three dimensional CIELAB color space. There are three axes: L* (defining light to dark); b* (defining blue to yellow); and a* (defining red to green). Any point in the three dimensional CIELAB color space may be defined by its L*, a*, and b* coordinates. The same point may also be defined by L*, hue angle, and chroma, which uses cylindrical coordinates. The hue angle is defined by the formula: $H_{ab}=\tan^{-1}(b^*/a^*)$, where a* and b* are coordinates in the L*a*b* three dimensional CIELAB color space. A detailed description of hue angle may be found in M. L. Gulrajani (Ed.), (2010). *Colour Measurement: Principles, Advances and Industrial Applications*. Cambridge, United Kingdom: Woodhouse Publishing, which is herein incorporated by reference in its entirety.

The one or more pigments of the oral care composition may be capable of reflecting sufficient light such that the treated teeth are perceivably whiter than their initial color. In some embodiments, the pigments may be colored such that its natural color is within the violet-red to green-blue color. More particularly, the pigment may be violet or blue (e.g., one of those listed in the Colour Index International). These pigments are listed as pigment violet 1 through to pigment violet 56 and pigment blue 1 through 83. In some embodiments, the pigment violets may be pigment violet 1, 1:1, 1:2, 2, 3, 5:1, 13, 19, 23, 25, 27, 31, 32, 37, 39, 42, 44, and 50. In some embodiments, the pigment blues may be pigment blue 1, 2, 9, 10, 14, 15, 15:1, 15:2, 15:3, 15:4, 15:6 16, 18, 19, 24:1, 25, 56, 60, 61, 62, and 66. Other suitable pigments may include, but are not limited to, pigment ultramarine blue and ultramarine violet. In an exemplary embodiment, the pigment is Pigment Blue 15, more typically the pigment is Pigment Blue 15:1, 15:2, 15:3, 15:4, 15:5 or 15:6, most typically 15:1.

While blue or violet single pigments may be used in the oral care composition, the same effect may be achieved through mixing pigments outside of the hue angle range of about 200 degrees to about 320 degrees. The desired hue angle may instead be obtained by mixing red and green-blue pigments to yield a blue or violet shaded pigment.

The amount of one or more of the pigments in the oral care composition may widely vary. For example, the amount of one or more of the pigments in the oral care composition may be from about 0.0006 wt %, about 0.0007 wt %, about 0.0008 wt %, about 0.0009 wt %, about 0.0010 wt %, about 0.0011 wt %, about 0.0012 wt %, about 0.0013 wt %, about 0.0014 wt %, about 0.0015 wt %, about 0.0016 wt %, about 0.0017 wt %, about 0.0018 wt %, or about 0.0019 wt % to about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %, about 0.0080 wt %, or greater. In another example, the amount of one or more of the pigments in the oral care composition may be about 0.0006 wt % to about 0.0022 wt %, about 0.0007 wt % to about 0.0021 wt %, about 0.0008 wt % to about 0.0020 wt %, about 0.0009 wt % to about 0.0019 wt %, about 0.0010 wt % to about 0.0018 wt %, about 0.0011 wt % to about 0.0017 wt %, about 0.0012 wt % to about 0.0016 wt %, or about 0.0013 wt % to about 0.0015 wt %. In another example, the amount of one or more of the pigments in the oral care composition may be about 0.0010 wt % to about 0.0090 wt %, about 0.0020 wt % to about 0.0080 wt %, about 0.0030 wt % to about 0.0070 wt %, or about 0.0040 wt % to about 0.0060 wt %. In another example, the amount of one or more of the pigments in the oral care composition may be about 0.00001 wt % to about 0.00015 wt %, about 0.00002 wt % to about 0.00014 wt %, about 0.00003 wt % to about 0.00013 wt %, about 0.00004 wt % to about 0.00012 wt %, about 0.00005 wt % to about 0.00011 wt %, about 0.00006 wt % to about 0.00010 wt %, or about 0.00007 wt % to about 0.00009 wt %.

In at least one embodiment, the one or more pigments may be disposed or dispersed uniformly throughout the oral care composition. In another embodiment, the one or more pigments may be disposed or dispersed in different phases of the oral care composition. For example, one or more of the pigments may be disposed or dispersed in a first phase (e.g., a hydrophobic phase) of the oral care composition, and one or more of the remaining pigments, or no pigment, may be disposed or dispersed in a second phase (e.g., a hydrophilic phase) of the oral care composition.

Dyes

As previously discussed, the oral care composition may include one or more dyes. The dyes may include any organic species that is substantially or essentially water soluble in an aqueous solution or medium in which the dye remains chemically stable. It should be appreciated, however, that some dyes may be soluble in an oil or hydrophobic phase. For example, D&C Green No. 6 may be at least partially soluble in a hydrophobic phase of the oral care composition. The one or more dyes may be configured to enhance the whiteness of the teeth. For example, the dyes may be deposited on the surface of the teeth to alter the visually perceived whiteness thereof. The dyes may generally be capable of reflecting sufficient light such that the treated teeth are perceivably whiter than its initial color (e.g., via spectrophotometric methods). Preferably, the one or more dyes are colored such that its natural color is within the violet-red to green-blue color, more preferably from a violet color to a blue color.

The one or more dyes may have a hue angle, in the CIELAB scale, of from about 200 degrees to about 320 degrees. For example, at least one of the dyes may have a hue angle of from about 200 to about 320 degrees. In another example, the one or more dyes may be contacted, mixed, or otherwise combined with one another to yield a hue angle of from about 200 degrees to about 320 degrees. In an exemplary embodiment, the dyes may have a hue angle between about 250 and about 290 degrees.

In a preferred embodiment, one or more of the dyes are water soluble. As used herein, the term "water-soluble dye"

may refer to dyes having an aqueous solubility of at least 10 g/L at 25° C., more preferably at least 100 g/L at 25° C., where the solubility is determined in un-buffered distilled water. The dyes may be or include, but are not limited to, triarylmethane dyes, especially anionic triphenylmethane dyes, such as diaminotriphenylmethane dyes containing from two to four sulphonate groups. A detailed description of triarylmethane dyes may be found in PCT Publication No. WO 2015/095709 to Colgate-Palmolive Company, which is herein incorporated by reference in its entirety.

The dyes may include any food color additives presently certified under the Food Drug & Cosmetic Act for use in food and ingested drugs. Illustrative dyes may include, but are not limited to, FD&C Blue No. 1 (Color Index [CI] 42090; CAS No. 3844-45-9), FD&C Blue No. 2 (CI 73015; CAS No. 860-22-0), CI Food Blue 5 or Acid Blue 3 (CI 42051; CAS No. 3536-49-0), Acid Blue 9 (CI 42090; CAS No. 2650-18-2), Acid Blue 1 (CI 42045; CAS No. 129-17-9), D&C Green No. 6 (CI 61565; CAS No. 128-80-3), D&C Violet No. 2 (CI 60725; CAS No. 81-48-1), D&C Green No. 5 (CI 61570; CAS No. 4403-90-1), D&C Orange No. 5 (CI 45370; CAS No. 596-03-2), D&C Red No. 21 (CI 45380; CAS No. 15086-94-9), D&C Red No. 22 (CI 45380; CAS No. 548-26-5), D&C Red No. 27 (CI 45410; CAS No. 13473-26-2), D&C Red No. 28 (CI 45410; CAS No. 18472-87-2), D&C Red No. 30 (CI 73360; CAS No. 2379-74-0), D&C Red No. 40 (CI 16035; CAS No. 25956-17-6), D&C Yellow No. 10 (CI 47005; CAS No. 68814-04-0), FD&C Yellow No. 5 (CI 19140; CAS No. 1934-21-0), FD&C Yellow No. 6 (CI 15985; CAS No. 2783-94-0), FD&C Green No. 3 (CI 42053; CAS No. 2353-45-9), FD&C Red No. 3 (CI 45430; CAS No. 16423-68-0), or the like, and combinations or mixtures thereof in varying proportions. In a preferred embodiment, the oral care composition includes at least one of CI Food Blue 5, FD&C Blue No. 1, D&C Green No. 6, and D&C Violet No. 2.

The amount of one or more of the dyes in the oral care composition may widely vary. For example, the amount of one or more of the dyes in the oral care composition may be from about 0.0006 wt %, about 0.0007 wt %, about 0.0008 wt %, about 0.0009 wt %, about 0.0010 wt %, about 0.0011 wt %, about 0.0012 wt %, about 0.0013 wt %, about 0.0014 wt %, about 0.0015 wt %, about 0.0016 wt %, about 0.0017 wt %, about 0.0018 wt %, or about 0.0019 wt % to about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %, about 0.0080 wt %, or greater. In another example, the amount of one or more of the dyes in the oral care composition may be about 0.0006 wt % to about 0.0022 wt %, about 0.0007 wt % to about 0.0021 wt %, about 0.0008 wt % to about 0.0020 wt %, about 0.0009 wt % to about 0.0019 wt %, about 0.0010 wt % to about 0.0018 wt %, about 0.0011 wt % to about 0.0017 wt %, about 0.0012 wt % to about 0.0016 wt %, or about 0.0013 wt % to about 0.0015 wt %. In another example, the amount of one or more of the dyes in the oral care composition may be about 0.0010 wt % to about 0.0090 wt %, about 0.0020 wt % to about 0.0080 wt %, about 0.0030 wt % to about 0.0070 wt %, or about 0.0040 wt % to about 0.0060 wt %. In another example, the amount of one or more of the dyes in the oral care composition may be about 0.00001 wt % to about 0.00015 wt %, about 0.00002 wt % to about 0.00014 wt %, about 0.00003 wt % to about 0.00013 wt %, about 0.00004 wt % to about 0.00012 wt %, about 0.00005 wt % to about 0.00011 wt %, about 0.00006 wt % to about 0.00010 wt %, or about 0.00007 wt % to about 0.00009 wt %.

In at least one embodiment, the one or more dyes may be disposed or dispersed uniformly throughout the oral care composition. In another embodiment, the one or more dyes may be disposed or dispersed in different phases of the oral care composition. For example, one or more of the dyes may be disposed or dispersed in a first phase (e.g., a hydrophobic phase) of the oral care composition, and one or more of the remaining dyes, or no dye, may be disposed or dispersed in a second phase (e.g., a hydrophilic phase) of the oral care composition.

Whitening Efficacy

In some embodiments, the oral care composition disclosed herein has a whitening efficacy relatively greater than the whitening efficacy of a comparative or conventional oral care composition, which may include the same ingredients as the oral care composition of the present disclosure, except that the comparative composition does not contain zinc. As used herein, the phrase "whitening efficacy" is intended to refer to the amount of change in tooth color. The color change may be measured according to the L*a*b* color scale. The luminance or lightness (L*) value measures brightness and varies from a value of one hundred for perfect white to zero for black, assuming a* and b* are zero. The a* value is a measure of redness when positive, gray when zero and greenness when negative. The b* value is a measure of yellowness when positive, gray when zero and blueness when negative. Generally, teeth appear whiter as: the L* value increases meaning they become brighter, the a* value increases or decreases, depending upon whether the stained teeth have a green tint or red tint prior to whitening, and the b* value decreases meaning they become less yellow. While this is the general relationship for perceived whitening, the b* value might also slightly increase if the magnitude of the increase of the L* value is large enough. Similarly, the L* value might also decrease if the magnitude of the decrease of the b* value is large enough to overshadow the less significant change in L*.

In some embodiments, a whitening index (WIO) is used to assess tooth whiteness. The whiteness index is based on the distance of a color value from a nominal white point, represented in the CIELAB colour space as $L^*=100$, $a^*=0$ and $b^*=0$. Changes in the whitening index may be used to assess the whitening efficacy (ΔWIO) of a composition before and after a treatment. The whitening efficacy (ΔWIO) may be calculated according to formula (1), as described in Joiner et al., "A Review of Tooth Colour and Whiteness", Journal of Dentistry, 2008, 36S:S2-S7, the disclosure of which is incorporated herein by reference in its entirety.

$$\Delta WIO = WIO(\text{Treatment}) - WIO(\text{baseline}) \qquad (1)$$

Whitening efficacy of a composition may be determined by any method known in the art. For example, human teeth or polished hydroxyapatite discs may be rinsed in water and brushed before baseline color measurements are made (using, for example, a Minolta chromameter CR300). The brushing may be performed using a brushing machine. The brushed discs may then be soaked in sterile human saliva for 15 minutes, and then treated with (i) a composition of the present disclosure or (ii) a comparative composition. After treatment, the discs may be rinsed with about 100 mL of water, and the color of the discs may then be re-measured. The change in L*, a*, and b* may be recorded for both treatment (i) and treatment (ii) and the WIO and ΔWIO values calculated. From a comparison of these data, any whitening efficiency of a composition is readily seen. Other methods for assessing whitening efficacy are described in the Examples, herein below.

Whitening Agents

As used herein, a "whitening agent" may refer to a substance or material that effects whitening to the surfaces of teeth to which it is applied. Illustrative whitening agents may include, but are not limited to oxidizing agents, reducing agents, or combinations thereof. For example, whitening agents may include peroxides and bleaching ingredients. In at least one embodiment, the oral care composition disclosed herein may not include any, or may be free of, one or more whitening agent, such as the peroxides or peroxide compounds and/or the bleaching ingredients. In a preferred embodiment, the oral care composition disclosed herein may be free or substantially free of all of the whitening agents. Bleaching ingredients may include chlorites and hypochlorites. Examples of chlorites and hypochlorites include those having alkali or alkaline metal cations, such as calcium chlorite, barium chlorite, magnesium chlorite, lithium chlorite, sodium chlorite, potassium chlorite, calcium hypochlorite, barium hypochlorite, magnesium hypochlorite, lithium hypochlorite, lithium hypochlorite, and sodium hypochlorite.

The "peroxide" or "peroxide compound" may be an oxidizing compound comprising a bivalent oxygen-oxygen group. Peroxide compounds include peroxides and hyperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and mixtures thereof. Peroxy acids and their salts include organic peroxy acids such as alkyl peroxy acids, and monoperoxyphthalate, and mixtures thereof, as well as inorganic peroxy acid salts such as persulfate, dipersulfate, percarbonate, perphosphate, perborate, and persilicate salts of alkali and alkaline earth metals such as lithium, potassium, sodium, magnesium, calcium, and barium, and mixtures thereof. The peroxide compound may include hydrogen peroxide, urea peroxide, sodium percarbonate or mixtures thereof.

As used herein, the term "reducing agent" may refer to compounds that may donate an electron to another molecule in the environment of the oral cavity without having a deleterious or unacceptably harmful affect on the oral cavity in normal and accepted use. Synonyms for this term are preservatives, anti-oxidizing agents, or antioxidants. There are numerous compounds which have been proven to be useful as reducing agents. A list of such compounds currently recognized for this purpose may be found in reference manuals and compendia covering pharmaceutical and oral care products. Illustrative reducing agents may include, but are not limited to, vitamin C and its esters, citric acid, vitamin E, the benzoates and hydroxybenzoates, butylated hydroxytoluene (BHT), butylated hydroxyanisole (BHA) and other reducing phenols, derivatives of dihydroxyquinoline, derivatives of polymerized 2,2,4-trimethyl-1,2-dihydroquinoline and alkyl gallate such as dodecyl gallate, ethyl gallate, octyl gallate, and propyl gallate. In some embodiments, vitamin C, vitamin E, BHA, BHT, propyl gallate, and combinations thereof are used in the oral care composition.

As discussed above, in a preferred embodiment, the oral care composition may be free or substantially free of one or more of the whitening agents, such as the peroxides or peroxide compounds and/or the bleaching ingredients. As used herein, the terms "free" or "substantially free" may refer to a composition that contains less than 0.1 wt %, less than 0.05 wt %, less than 0.01 wt %, less than 0.005 wt %, or less than 0.0001 wt %. Accordingly, the tooth whitening effect of the oral care composition may be provided by the blue dye and/or the blue pigment rather than by the presence of any whitening agents. For example, the tooth whitening effect of the oral care composition may be provided by the presence of zinc in combination with the dye and/or the pigments, rather than by the presence of any peroxide whitening agents.

Vehicle

The oral care composition may form at least a portion of or be used in one or more oral care products. Illustrative oral care products may include, but are not limited to, a toothpaste (dentifrice), a prophylactic paste, a tooth powder, a tooth polish, a tooth gel, a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In an exemplary embodiment, the oral care composition may form at least a portion of or be used in a mouthwash. For example, the oral care composition may include or be combined with an orally acceptable vehicle to form the oral care product (e.g., the mouthwash). In an exemplary embodiment, the orally acceptable vehicle may include a mixture of water, glycerin, and sorbitol. In at least one embodiment, the orally acceptable vehicle may include water and glycerin. In a preferred embodiment, the oral care composition is combined with an orally acceptable vehicle including a hydrophilic phase and a hydrophobic phase, and optionally a hydrotrope to form a dual-phase mouthwash or a dual-phase mouthwash composition. The hydrophilic phase and the hydrophobic phase of the oral care composition may be agitated or mixed to form a temporary oil-in-water emulsion that separates back into the hydrophobic and hydrophilic phases within five seconds to one hour after mixing.

The hydrophobic phase of the oral care composition may contain any orally acceptable hydrophobic liquid (e.g., generally recognized as safe). The orally acceptable hydrophobic liquids may include, but are not limited to, isopropyl myristate, mineral oil (e.g., white mineral oil, liquid paraffin, etc.), edible oils, or the like, or any combination thereof. Illustrative edible oils may include olive oil, corn oil, coconut oil, soybean oil, and combinations thereof. The hydrophobic phase may have an HLB of from 7 to 12, preferably an HLB of about 10. A preferred hydrophobic phase comprises heavy white mineral oil.

The hydrophilic phase of the oral care composition may be an aqueous or water based phase. For example, the hydrophilic phase may have from about 40 wt % to about 95 wt % water. The hydrophilic phase may also include orally acceptable alcohols, humectants, and/or polymers. A humectant, on a pure humectant basis, may generally include about 10 wt % to about 50 wt %, or about 15 wt % to about 25 wt % of the oral care composition.

The hydrophilic phase may optionally include one or more polymers. Illustrative polymers that may be included in the hydrophilic phase may include polyvinylmethyl ether maleic acid copolymers, polysaccharides (e.g., cellulose derivatives, polysaccharide gums, etc.). The cellulose derivatives may include carboxymethyl cellulose, and the polysaccharide gums may include xanthum gum or carrageenan gum). In at least one embodiment, the hydrophilic phase may include one or more copolymers, such as a polyvinylmethylether/maleic anhydride (PVM/MA) copolymer. An illustrative PVM/MA copolymer may include those under the GANTREZ® brand from ISP of Wayne, N.J. In another embodiment, the hydrophilic phase may be free or substantially free of PVA/MA copolymers, such as GANTREZ®.

As discussed above, the dual-phase mouthwash, including the hydrophilic phase and the hydrophobic phase, may optionally include a hydrotrope. The hydrotrope may include compounds that solubilize hydrophobic compounds in aqueous solutions. The hydrotrope may be a low molecular weight amphiphilic compound having a hydrophilic functional group and a low molecular weight hydrophobe. The hydrophobic functional group may attach to an organic moiety of the hydrophobic compounds to facility the solubility thereof in the aqueous solutions. Illustrative hydrotropes of the oral care composition and the dual-phase mouthwash may include, but are not limited to, aromatic sulfonates, aromatic phosphate esters, glycerin, di and polycarboxylates, polyglycols, and alcohols, including polyhydric alcohols.

The hydrotropes may have an HLB of from about 7 to about 18. The hydrotrope may have an HLB similar to that of the hydrophobic phase; and thus, the exact hydrotrope utilized in the oral care composition will be dependent upon the hydrophobic phase. Preferably, the HLB of the hydrotrope is greater than the HLB of the hydrophobic phase. For example, the HLB of the hydrotrope may be about 10%, about 15%, about 20%, or about 30% greater than the HLB of the hydrophobic phase. In an exemplary embodiment, the dual-phase mouthwash or the oral care composition thereof may include one or more polyglycols and/or pylyhydric alcohols, preferably a diol and/or a triol. In a preferred embodiment, the hydrotropes may include propylene glycol. In another embodiment, the hydrotropes may include glycerin and propylene glycol. It should be appreciated that the hydrotropes lack surfactant properties. Accordingly, the dispersion of the hydrophobic or oil phase in the hydrophilic or water phase may not be thermodynamically stable. Thus, the emulsion formed by the agitation or mixing of the hydrophobic and hydrophilic phases is temporary.

Antifoam Agent

The oral care composition may include one or more antifoam agents. Illustrative antifoam agents may include Antifoam 1520-US from DOW CORNING® of Midland, Mich., and may include polydimethylsiloxane, tristearate, glyceryl monostearate, methylcellulose, EO glycol, silica, xantham gum, benzoic acid, and sulfuric acid. The amount of the antifoam agent in the oral care composition may be less than 0.008 wt %, less than 0.007 wt %, less than 0.006 wt %, less than 0.005 wt %, or less than 0.004 wt %.

Fluoride Ion Source

The oral care composition may further include one or more fluoride ion sources (e.g., soluble fluoride salts). A wide variety of fluoride ion-yielding materials may employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a preferred embodiment, the fluoride ion source includes sodium fluoride. The amount of the fluoride ion source in the oral care composition may be less than 0.08 wt %, less than 0.07 wt %, less than 0.06 wt %, less than 0.05 wt %, or less than 0.04 wt %. For example, the amount of the fluoride ion source may be about 0.05 wt %. In another embodiment, the fluoride ion source is present in an amount to provide a total of about 100 to about 20,000 ppm, about 200 to about 5,000 ppm, or about 500 to about 2,500 ppm, fluoride ions.

Surfactants

The oral care composition may include one or more surfactants. For example, the oral care composition may include one or more anionic surfactants, one or more cationic surfactants, one or more zwitterionic surfactants, one or more nonionic surfactants, and mixtures thereof. Examples of suitable surfactants may be found in U.S. Pat. No. 3,959,458 to Agricola et al., U.S. Pat. No. 3,937,807 to Haefele, and U.S. Pat. No. 4,051,234 to Gieske et al., the disclosures of which are incorporated herein by reference.

In at least one embodiment, the oral care composition includes at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6\text{-}30}$ alkyl. For example, in a preferred embodiment the anionic surfactant is sodium lauryl sulfate. The anionic surfactants may also include higher alkyl-ether sulfates. For example, the anionic surfactants may have a formula $CH_3(CH_2)_m CH_2 (OCH_2CH_2)_n OSO_3 X$, where m is 6-16, n is 1-6, and X is Na or K. In an exemplary embodiment, m is 10, and n is 2, 3, or 4, and X is Na or K. For example, the anionic surfactant may be sodium laureth-2 sulfate $(CH_3(CH_2)_{10}CH_2 (OCH_2CH_2)_2 OSO_3 Na)$. In another embodiment, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sultanate, sulthcolaurate (N-2-ethyl laurate potassium sulfoacetamide) and sodium lauryl sarcosinate. In an exemplary embodiment, the anionic surfactant is a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In at least one embodiment, the oral care composition may also include at least one nonionic surfactant. Accordingly, the oral care composition may include at least one anionic surfactant, at least one nonionic surfactant, or both an anionic surfactant and a nonionic surfactant. The nonionic surfactant may function as an emulsifier. Illustrative nonionic surfactants may include, but are not limited to, poloxamers or the like. For example, the nonionic surfactants may include polysorbate 20, poloxamer 407, poloxamer 338, or the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred embodiment, the nonionic surfactant is PEG 40 hydrogenated castor oil, which is commercially available as CREMOPHOR® RH40 from BASF Corp. of Florham Park, N.J.

The amount of any one or more of the surfactants in the oral care composition may be from about 0.010 wt %, about 0.020 wt %, about 0.030 wt %, about 0.040 wt %, about 0.045 wt %, about 0.049 wt %, or about 0.050 wt % to about 0.051 wt %, about 0.055 wt %, about 0.060 wt %, about 0.065 wt %, about 0.070 wt %, about 0.075 wt %, about 0.080 wt %, or greater. In another example, the amount of any one or more of the surfactants in the oral care composition may be about 0.010 wt % to about 0.090 wt %, about 0.020 wt % to about 0.080 wt %, about 0.030 wt % to about 0.070 wt %, about 0.040 wt % to about 0.060 wt %, about 0.045 wt % to about 0.055 wt %, or about 0.050 wt % to about 0.051 wt %. In yet another example, the amount of any one or more of the surfactants in the oral care composition may be greater than 0.010 wt %, greater than 0.020 wt %, greater than 0.030 wt %, greater than 0.040 wt %, greater than 0.045 wt %, greater than 0.049 wt %, or greater than 0.050 wt %. The amount of any one or more of the surfactants in the oral care composition may also be from about 0.10 wt %, about 0.20 wt %, about 0.30 wt %, about 0.40 wt %, about 0.45 wt %, about 0.49 wt %, or about 0.50 wt % to about 0.51 wt %, about 0.55 wt %, about 0.60 wt %, about 0.65 wt %, about 0.70 wt %, about 0.75 wt %, about 0.80 wt %, or greater. In another example, the amount of any one or more of the surfactants in the oral care composition may be about 0.10 wt % to about 0.90 wt %, about 0.20 wt % to about 0.80 wt %, about 0.30 wt % to about 0.70 wt %, about 0.40 wt % to about 0.60 wt %, about 0.45 wt % to about 0.55 wt %, or about 0.50 wt % to about 0.51 wt %. In yet another example, the amount of any one or more of the surfactants in the oral care composition may be greater than 0.10 wt %, greater than 0.20 wt %, greater than 0.30 wt %, greater than 0.40 wt %, greater than 0.45 wt %, greater than 0.49 wt %, or greater than 0.50 wt %.

In at least one embodiment, the oral care composition includes at least one anionic surfactant and at least one nonionic surfactant. For example, the surfactant in the oral care composition may include sodium lauryl sulfate, poloxamer 407, and poloxamer 338. In a preferred embodiment, the surfactant in the oral care composition includes sodium lauryl sulfate in an amount of about 0.050 wt %, poloxamer 407 in an amount of about 0.50 wt %, poloxamer 338 in an amount of about 0.50 wt %, and PEG-40 hydrogenated castor oil in an amount of about 0.100 wt %. It should be appreciated, however, that the oral care composition may not include the anionic surfactant. For example, the oral care composition may omit at least the sodium lauryl sulfate.

Flavoring Agents

The oral care composition may also include one or more flavoring agents. Illustrative flavoring agents may include, but are not limited to, essential oils and various flavoring aldehydes, esters, alcohols, and the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones and mixtures thereof. Examples of the essential oils include oils of spearmint, peppermint, wintergreen, sassafras, clove, sage, eucalyptus, marjoram, cinnamon, lemon, lime, grapefruit, and orange. In another example, the flavoring agents may include menthol, carvone, and anethole. In a preferred embodiment, the flavoring agent includes peppermint and spearmint. In a more preferred embodiment, the flavoring agent includes a Firmenich Newman Flavor. The amount of the flavoring agent in the oral care composition may be less than 1.0 wt %, less than 0.9 wt %, less than 0.8 wt %, or less than 0.7 wt %. For example, the amount of the flavoring agent in the oral care composition may be about 0.0 wt % to about 1.0 wt %, about 0.5 wt % to about 0.9 wt %, about 0.7 wt % to about 0.8 wt %. In a preferred embodiment, the amount of the flavoring agent in the oral care composition is about 0.75 wt % to about 0.80 wt %.

Chelating and Anti-Calculus Agents

The oral care composition may optionally include one or more chelating agents and/or one or more anti-plaque agents. The chelating agents may be capable or configured to form complexes or bind with calcium found in cell walls of bacteria to weaken the cell walls and enhance or augment bacterial lysis. Illustrative anti-calculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, and diphosphonates. Illustrative chelating or anti-calculus agents may also include soluble pyrophosphates salts. In a preferred embodiment, the pyrophosphate salts of the oral care composition may be or include a alkali metal pyrophosphate salt. Illustrative alkali metal pyrophosphate salts include tetra alkali metal pyrophosphate, dialkali metal diacid pyrophosphate, trialkali metal monoacid pyrophosphate, and mixtures thereof, where the alkali metals are sodium or potassium. For example, in a preferred embodiment, the alkali metal pyrophosphate salts may be or include tetrasodium pyrophosphate and/or tetrapotassium pyrophosphate. The alkali metal pyrophosphate salts may be in either a hydrated form or a non-hydrated form.

The chelating or anti-plaque agents may be present in the oral care composition in an effective amount. For example, an effective amount of the pyrophosphate salt may generally be an amount that provides at least 0.5 wt % of the pyrophosphate ions in the oral care composition. In another example, an effective amount of the pyrophosphate salt may generally be an amount that provides at about 0.9 wt % to about 3.0 wt % of the pyrophosphate ions in the oral care composition. In yet another example, an effective amount of the pyrophosphate salt may generally be an amount that provides at about 0.30 wt % to about 1.40 wt % of the pyrophosphate ions in the oral care composition. The amount of the chelating or anti-plaque agents in the oral care composition may be from about 0.30 wt %, about 0.35 wt %, about 0.40 wt %, about 0.45 wt %, about 0.50 wt %, about 0.55 wt %, or about 0.60 wt % to about 0.90 wt %, about 0.95 wt %, about 1.00 wt %, about 1.05 wt %, about 1.10 wt %, about 1.15 wt %, about 1.20 wt %, about 1.25 wt %, about 1.30 wt %, about 1.35 wt %, or about 1.40 wt %. In an exemplary embodiment, the oral care composition is free or substantially free of the chelating or anti-plaque agents. For example, the oral care composition is free or substantially free of tetrasodium pyrophosphate and/or tetrapotassium pyrophosphate.

Water

The oral care composition may include water. Water of the oral care composition may be deionized and free of organic impurities. Water may make up the balance of the oral care composition. For example, the amount of water in the oral care composition may be from about 10 wt % to 90 wt %, about 40 wt % to about 85 wt %, or about 60 wt % to about 80 wt %. In another example, the amount of water in the oral care composition may be at least 60 wt %, at least 65 wt %, at least 70 wt %, at least 78 wt %, or at least 79 wt %. The amount of water in the oral care composition may include free water added and water introduced with other components or materials of the oral care composition. For example, the amount of the water in the oral care composition may include free water and water associated with the humectants, flavoring agents, or any other component of the oral care composition.

Humectants

As previously discussed, the oral care composition (e.g., the hydrophilic phase thereof) may include humectants. The humectants may be capable or configured to reduce evaporation and lower water activity. It should be appreciated that the humectants may also be capable of imparting desirable sweetness or flavor to the oral care composition. Illustrative humectants may include, but are not limited to polyhydric alcohols, such as glycerin, sorbitol, xylitol, propylene glycol, as well as other polyols, and mixtures thereof.

Other Ingredients

The oral care composition may optionally include one or more further ingredients. For example, the oral care composition may include one or more antimicrobial agents and/or one or more preservatives such as, methylisothiazolinone (MIT), sodium benzoate, potassium sorbate, benzyl alcohol, and combinations thereof. In another example, the oral care composition may include one or more antibacterial agents selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic anti septics, hexetidine, octenidine, sanguinarine, povidone iodine, delmopinol, salifluor, other metal ions (e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol, and other piperidino derivatives, nicin preparations, chlorite salts; and mixtures of any of the foregoing. In a preferred embodiment, the antibacterial agent includes cetylpyridinium chloride (CPC). For example, all of the dual-phase mouthwash compositions disclosed herein may include CPC as an antibacterial agent.

The oral care composition may optionally include one or more pH modifying agents. For example, the oral care composition may include one or more acidifying agents and/or one or more basifying agents to reduce and/or increase the pH, respectively. The oral care composition may also include one or more buffering agents to control or modulate the pH within a predetermined or desired range. In at least one embodiment, the acidifying, buffering, and/or buffering agents may be include in the oral care composition to provide the oral care composition with a pH between 2 to 10, 2 to 8, 3 to 9, 4 to 8, 6 to 10, or 7 to 9. Any orally acceptable pH modifying agent may be used, including without limitation carboxylic acid (e.g., citric acid), phosphoric acid, and sulfonic acid, acid salts (e.g., monosodium citrate, disodium citrate, monosodium malate, sodium dihydrogen phosphate, etc.), alkali metal hydroxides, such as sodium hydroxide, carbonates, such as sodium carbonate, bicarbonates, sesquicarbonates, borates, silicates, phosphates (e.g., monosodium phosphate, trisodium phosphate, pyrophosphate salts, etc.), imidazole, organic acids (e.g., lactic acid, etc.), and the like, and mixtures thereof. The one or more pH modifying agents may be optionally present in an amount effective to maintain the oral care composition in an orally acceptable pH range.

Methods

In various embodiments, the present disclosure provides methods to whiten the surface of the teeth in a human or animal subject. The method may include contacting the surface of the teeth with the oral care composition of the present disclosure. As used herein "animal subject" includes non-human mammals such as canines, felines, and horses. The whitening oral care composition may be contacted with an oral surface of the human or animal subject to thereby whiten teeth in a highly efficacious manner.

In various embodiments, the oral care composition prepared in accordance with the present disclosure may be applied regularly to an oral surface, for example on a daily basis, at least one time daily for multiple days, or alternately every second or third day. In some embodiments, the oral care composition is applied to the oral surfaces from 1 to 3 times daily, for at least 2 weeks up to 8 weeks, from four months to three years, or more, up to a lifetime.

In some embodiments, the oral care product (e.g., the mouthwash) or the oral care composition thereof may be applied directly to the teeth using a delivery device, such as a pen, (e.g., a COLGATE® whitening pen or a COLGATE® ACTIS™ whitening pen, Colgate-Palmolive Company, New York, N.Y.), a liquid stick having an applicator, such as a felt tip, brush, roller ball, or non-woven pad, sufficient to effect whitening.

Some embodiments provide a method wherein a delivery device, such as a whitening pen is stored within an oral care implement, such as a toothbrush. In some embodiments, the delivery device, such as a whitening pen is removed from the oral care implement prior to application of the composition to the tooth. In some embodiments, the composition is applied to the tooth after brushing with the oral care implement.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

EXAMPLES

Four mouthwashes were prepared by combining the ingredients/components according to Table 1. Particularly, the following mouthwashes were prepared: (1) a single phase mouthwash including 0.0014 wt % CI Food Blue 5 and 0.087 wt % Zn; (2) a dual-phase mouthwash including 0.0040 wt % CI Food Blue 5 and 0.00 wt % Zn; (3) a dual-phase mouthwash including 0.0014 wt % CI Food Blue 5, 0.00 wt % Zn, and 1.80 wt % polyphosphates; and (4) a dual-phase mouthwash including the oral care composition according to the present disclosure including 0.0014 wt % CI Food Blue 5 and 0.280 wt % Zinc L-lactate Dihydrate (about 0.066 wt % Zn).

TABLE 1

Compositions of Mouthwashes in Table 1

| Ingredient | (1) Single-Phase Mouthwash with Zn (Wt. %) | (2) Dual-Phase Mouthwash (Wt. %) | (3) Dual-Phase Mouthwash with Polyphosphates (Wt. %) | (4) Dual-Phase Mouthwash with Zn (Wt. %) |
|---|---|---|---|---|
| Water | 76.786 | 79.070 | 66.592 | 78.799 |
| Orally Acceptable Hydrophobic Liquids | — | 12.000 | 12.250 | 12.200 |
| Hydrotrope | 7.500 | 7.496 | 7.500 | 7.500 |
| Flavoring Agents | 5.670 | 1.180 | 6.350 | 0.940 |
| Humectants | 5.000 | — | 5.000 | — |
| Fluoride Ion Source | 0.050 | 0.500 | 0.050 | 0.050 |
| Antibacterial Agents | — | 0.050 | 0.075 | 0.075 |
| GANTREZ ® S-97 | 1.513 | — | — | — |
| Zinc L-lactate Dihydrate | — | — | — | 0.280 |
| Zinc Citrate Trihydrate | 0.280 | — | — | — |
| Polyphosphates | 1.80 | — | 1.80 | — |
| Preservatives | 0.100 | 0.100 | 0.100 | 0.100 |
| Buffering Agents | — | 0.0250 | — | — |
| Surfactants | 1.300 | 0.020 | — | — |
| Reducing Agents | — | 0.010 | — | — |
| pH Modifying Agents | — | — | 0.300 | 0.050 |
| CI Food Blue 5 (CI 42052) | 0.0014 | 0.0004 | 0.0014 | 0.0014 |
| D & C Green No. 6 | — | — | 0.000080 | 0.000080 |
| D & C Violet No. 2 (CI 60725) | — | 0.00012 | — | — |
| Antifoam Agent | — | — | — | 0.005 |
| Total | 100.000 | 100.000 | 100.000 | 100.000 |

Each of the mouthwashes was tested on a set of 16 human teeth. It is noted that the same set of teeth was used for each of the mouthwashes (1), (2), (3), and (4) to minimize experimental variability. Accordingly, prior to each testing cycle, the set of teeth was brushed with a silica toothpaste for 10 minutes, and a baseline or reference color was measured with a spectrophotometer. In each testing cycle, the set of teeth was soaked in saliva for 15 minutes in an aluminum tray. The set of teeth was then treated with one of the mouthwashes (1), (2), (3), and (4) by gently pouring the saliva out of the tray and off of the teeth, and adding 10 mL of the respective mouthwash (1), (2), (3), and (4) to the tray. It is noted that each of the dual-phase mouthwashes (2), (3), and (4) was first agitated to mix the hydrophobic and hydrophilic layers thereof prior to their addition to the tray. The tray containing the respective mouthwash (1), (2), (3), and (4) was then gently agitated to mimic or model the act of swishing. After one minute, the respective mouthwash (1), (2), (3), and (4) was poured out of the tray, and the set of teeth was rinsed with 100 mL of water. The CieLab values were then measured with a spectrophotometer, and the whitening efficacy (ΔWIO) was calculated as discussed above. The results of the whitening efficacy (ΔWIO) of each of the mouthwashes (1), (2), (3), and (4) are summarized below in Table 2.

TABLE 2

ΔWIO of Mouthwashes containing blue dye with and without zinc

| (1) Single-Phase Mouthwash with Zn (ΔWIO) | (2) Dual-Phase Mouthwash (ΔWIO) | (3) Dual-Phase Mouthwash with Polyphosphates (ΔWIO) | (4) Dual-Phase Mouthwash with Zn (ΔWIO) |
|---|---|---|---|
| 7.3 | 4.2 | 7.9 | 10.5 |

[93] As is evident from Table 2, when zinc is included in the oral care composition of the dual-phase mouthwash (4) the teeth exhibit increased retention of the blue dye on the surface or enamel thereof, thereby resulting in relatively increased whitening efficacy ΔWIO as compared to the dual-phase mouthwashes (2) (3) without the zinc. Additionally, when zinc is included in the oral care composition of the dual-phase mouthwash (4) the teeth exhibit increased retention of the blue dye on the surface or enamel thereof and increased whitening efficacy ΔWIO as compared to the single-phase mouthwash with zinc (1).

Accordingly, it has been surprisingly and unexpectedly discovered that the oral care composition, including the hydrophilic phase and the hydrophobic phase, the zinc, and the blue dye, when combined with one another, produce a dual-phase mouthwash that exhibits a synergistic effect and provides a significant and unexpected increase in whitening efficacy over conventional dual-phase oral care compositions without the zinc and over conventional single-phase oral care compositions with zinc.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:

1. A dual-phase mouthwash composition comprising:
   an orally acceptable vehicle comprising a hydrophilic phase and a hydrophobic phase;
   a blue dye and/or a blue pigment having a blue to blue-violet color with a hue angle in the CIELAB system from about 200 to about 320 degrees; wherein the blue dye and/or blue pigment comprises 0.0010 wt % to 0.0018% of CI Food Blue 5 and 0.00004 wt % to 0.00012 wt % of D&C Green No. 6; and a zinc salt comprising 0.25 wt % to 0.30 wt % zinc lactate; and cetylpyridinium chloride;

wherein all weight percentages are with respect to the total weight of the composition.

2. The dual-phase mouthwash composition of claim 1, wherein the zinc salt consists of a mixture of zinc lactate and zinc citrate.

3. The dual-phase mouthwash composition according to claim 1, wherein the dual-phase mouthwash composition comprises about 0.28 wt % of the zinc lactate.

4. The dual-phase mouthwash composition according to claim 1, wherein the zinc salt further comprises zinc citrate.

5. The dual-phase mouthwash composition according to claim 1, wherein the dual-phase mouthwash composition comprises 0.0012 wt % to 0.0016 wt % of the CI Food Blue 5.

6. The dual-phase mouthwash composition according to claim 1, wherein at least a portion of the CI Food Blue 5 dye is dispersed in the hydrophobic phase of the orally acceptable vehicle.

7. The dual-phase mouthwash composition according to claim 1, wherein at least a portion of the CI Food Blue 5 dye is dispersed in the hydrophilic phase of the orally acceptable vehicle.

8. The dual-phase mouthwash composition according to claim 1, wherein the blue dye and/or the blue pigment further comprises one of FD&C Blue No. 1 and D&C Violet No. 2.

9. The dual-phase mouthwash composition according to claim 1, wherein the hydrophobic phase comprises white mineral oil.

10. The dual-phase mouthwash composition according to claim 1, further comprising a fluoride ion source.

11. The dual-phase mouthwash composition according to claim 1, wherein the dual-phase mouthwash composition is free of peroxides.

12. The dual-phase mouthwash composition according to claim 1, further comprising a hydrotrope.

13. A method for whitening teeth comprising contacting the dual-phase mouthwash composition of claim 1 with a surface of the teeth.

14. The dual-phase mouthwash composition according to claim 10, wherein the fluoride ion source comprises sodium fluoride.

* * * * *